US012357925B2

(12) United States Patent
Prewer

(10) Patent No.: US 12,357,925 B2
(45) Date of Patent: Jul. 15, 2025

(54) AFFINITY CHROMATOGRAPHY

(71) Applicant: SWEDISH BIOMIMETICS 3000 LTD, Hethel (GB)

(72) Inventor: Andrew Richard Russell Prewer, Norfolk (GB)

(73) Assignee: NOVA PRIMARY MANUFACTURING LIMITED, Leicester (GB)

( * ) Notice: Subject to any disclaimer, the term of this patent is extended or adjusted under 35 U.S.C. 154(b) by 1205 days.

(21) Appl. No.: 16/967,307

(22) PCT Filed: Feb. 5, 2019

(86) PCT No.: PCT/GB2019/050302
§ 371 (c)(1),
(2) Date: Aug. 4, 2020

(87) PCT Pub. No.: WO2019/150137
PCT Pub. Date: Aug. 8, 2019

(65) Prior Publication Data
US 2021/0031124 A1  Feb. 4, 2021

(30) Foreign Application Priority Data

Feb. 5, 2018 (GB) .................................... 1801842

(51) Int. Cl.
| | |
|---|---|
| *B01D 15/38* | (2006.01) |
| *B01D 15/20* | (2006.01) |
| *B01D 15/22* | (2006.01) |
| *B01J 20/283* | (2006.01) |
| *B01J 20/285* | (2006.01) |
| *C07K 1/22* | (2006.01) |
| *G01N 30/02* | (2006.01) |
| *G01N 30/60* | (2006.01) |

(52) U.S. Cl.
CPC ........... *B01D 15/22* (2013.01); *B01D 15/203* (2013.01); *B01D 15/3804* (2013.01); *B01J 20/283* (2013.01); *B01J 20/285* (2013.01); *C07K 1/22* (2013.01); *G01N 30/60* (2013.01); *G01N 2030/027* (2013.01)

(58) Field of Classification Search
CPC ........ C07K 1/22; B01D 15/203; B01D 15/22; B01D 15/3804; G01N 30/60; G01N 30/88; G01N 2030/027; B01J 20/283; B01J 20/285
See application file for complete search history.

(56) References Cited

U.S. PATENT DOCUMENTS

| | | |
|---|---|---|
| 2008/0090995 A1 | 4/2008 | Andersson |
| 2010/0120636 A1 | 5/2010 | Prewer |
| 2010/0190974 A1 | 7/2010 | Prewer |
| 2016/0009762 A1 | 1/2016 | Gagnon |

FOREIGN PATENT DOCUMENTS

| | | |
|---|---|---|
| EP | 0611066 | 8/1994 |
| FR | 2831837 | 5/2003 |
| GB | 2192403 | 1/1988 |
| JP | H0810507 A | 1/1996 |
| JP | 2003066021 | 3/2003 |
| JP | 2014147928 A | 8/2014 |
| WO | 2017122009 | 7/2017 |

OTHER PUBLICATIONS

Opinion from Korean Patent Application No. 10-2020-7024153 dated Mar. 28, 2022 (w/English translation).
Office Action from Japanese Application No. 2020-539697 dated Sep. 7, 2022.
Search Report from Japanese Application No. 2020-539697 dated Sep. 14, 2022.
Examination Report from Chinese Application No. 201980011947.3 dated Mar. 24, 2022.
Hughes, "Method for Continuous Purification of Biological Material Using Immunosorbent," Biotechnology and Bioengineering Vo. XXI, pp. 1439-1455 (1979).
Search Report and Written Opinion from Application No. PCT/GB2019/050302 dated May 9, 2019 (11 pages).
UKIPO Search Report from Application No. GB1801842.4 dated Jun. 28, 2018 (3 pages).
Saraswat, et al., "Preparative Purification of Recombinant Proteins: Current Status and Future Trends," Biomed Research International vol. 2013.
Ongkudon, et al., "Chromatographic Removal of Endotoxins: A Bioprocess Engineer's Perspective," ISRN Chromatography vol. 2012, Article ID 649746.
Burnouf, et al., "Affinity Chromatography in the Industrial Purification of Plasma Proteins for Therapeutic Use," J. Biochem. Biophys. Methods 49 (2001) 575-586.
Chen, et al., "Preparation and Evaluation of Monolithic Molecularly Imprinted Sationary Phase for S-naproxen," J Pharm Anal vol. 1, No. 1 (2011) pp. 26-31.
Litvak, et al., "The Synthesis and Properties of the Sepharose-Bound tRNA Nucleotidyltransferase," Eur J Biochem 24 (1971) pp. 249-251.
Mierau, et al., "Industrial-Scale Production and Purification of a Heterologous Protein in Lactococcus lactis Using the Nisin-Controlled Gene Expression System NICE: The Case of Lysostaphin," Microbial Cell Factories, 2005 4:15.
Boyer, "Purification of Milk Whey a-Lactalbumin by Immobilized Metal-Ion Affinity Chromatography," Journal of Chemical Education, vol. 68 no. 5, May 1991, pp. 430-432.
Forier, et al., "DNA Aptamer Affinity Ligands for Highly Selective Purification of Human Plasma-Related Proteins from Multiple Sources," Journal of Chromatography A, 1489 (2017) pp. 39-50.

(Continued)

*Primary Examiner* — Shafiqul Haq
(74) *Attorney, Agent, or Firm* — Troutman Pepper Locke LLP; Ryan A. Schneider; Stephanie J. Remy

(57) ABSTRACT

This invention relates to a method of removing a chemical entity from a liquid using affinity chromatography. The method involves passing an elongate solid phase through a conduit through which the liquid also flows.

14 Claims, 1 Drawing Sheet

(56) References Cited

OTHER PUBLICATIONS

Wang, et al., "Antibody Purification Using Affinity Chromatography: A Case Study with Monoclonal Antibody to Ractopamine," Journal of Chromatography B, 971 (2014) pp. 10-13.
Gagnon, Pete, "Technology Trends in Antibody Purification," Journal of Chromatography A, 1221 (2012) pp. 57-70.
Arora, et al., "Affinity Chromatography: A Versatile Technique for Antibody Purification," Methods 116 (2017) pp. 84-94.
"Large-Scale Affinity," Biotechnology (Dec. 1987) vol. 5 pp. 1290-1293.

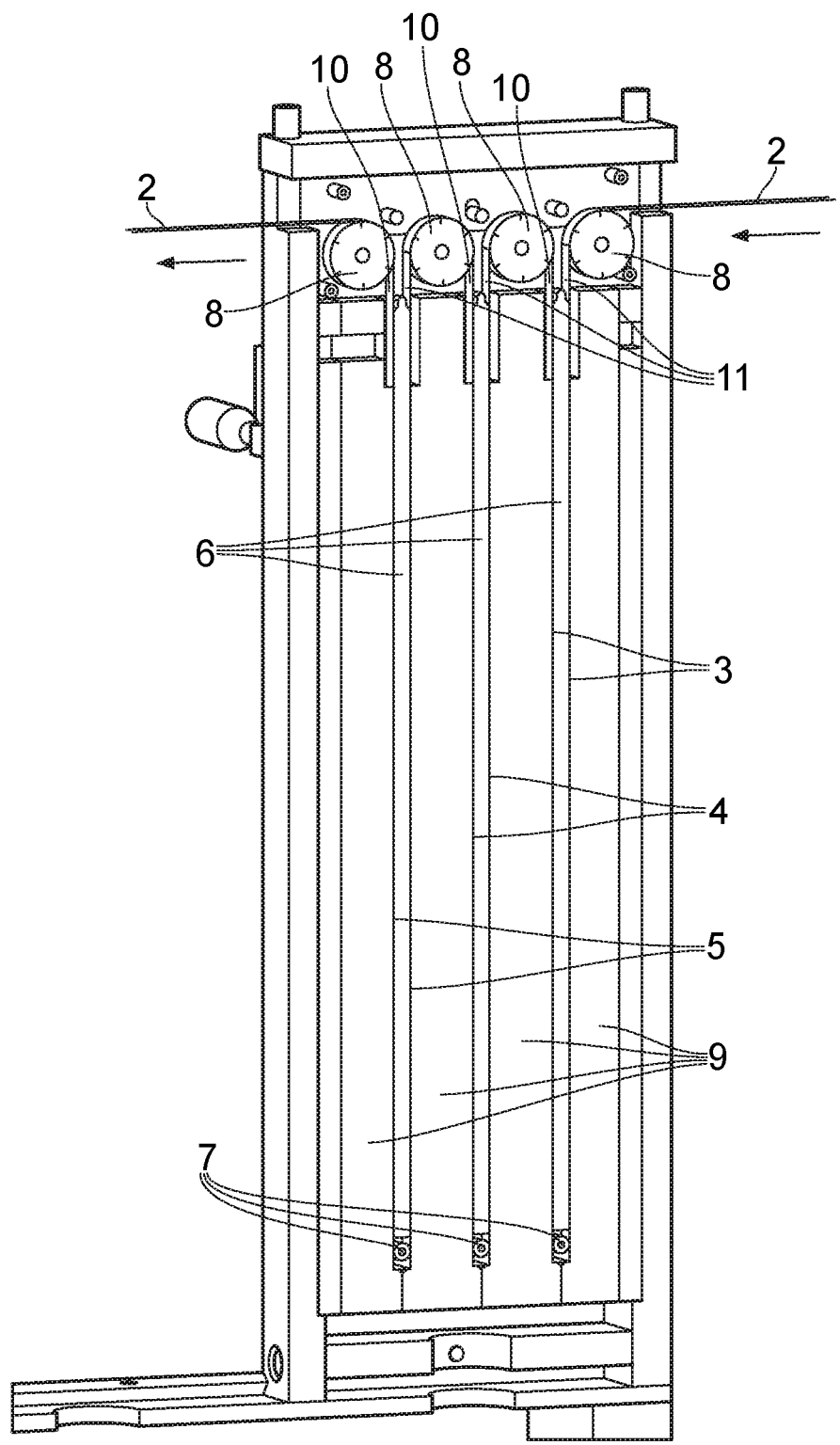

AFFINITY CHROMATOGRAPHY

This invention relates to a method of removing a chemical entity from a liquid using affinity chromatography. The method involves passing an elongate solid phase through a conduit through which the liquid also flows.

BACKGROUND

Biomolecules such as proteins, nucleic acids, antibodies, peptides and oligosaccharides are highly versatile biological materials with applications in medicine, testing and industrial processing. The new generation of biologic pharmaceuticals has produced a variety of novel therapies for many serious diseases that were previously considered hard or impossible to treat. These proteins and antibodies are typically produced in sterile fermenters using cells fed on inexpensive nutrients such as sugars and amino acids. Alternative methods of producing proteins have also been developed through the use of genetically modified plants and animals. Although the actual production of the materials using cell cultures, plants or animals is efficient, it has the drawback that the product is obtained in a dilute aqueous solution combined with a large amount of cellular by-products. This means that the actual purification of the raw material typically accounts for about more than 80% of the production cost.

The chief method for purifying proteins and antibodies uses a technique called 'affinity chromatography'. This uses a solid material that has been engineered to adsorb specifically the desired material. In this process the cellular mixture is mixed with the solid, and then the solid is separated, washed, and finally treated with a material that displaces the protein from the solid so it can be collected in the liquid for further processing.

Batch process affinity chromatography often achieves high outputs only when performed on a large scale. It also suffers from long cycle times and is plant intensive. The need for larger equipment means that hold times are extended, meaning that some products may degrade during manufacture leading to increased impurities and/or lowered yields. The development and validation of large scale chromatography processes is also expensive and time consuming.

Proteins, for example, are often produced by fermentation. The volumes of liquid produced during the fermentation stage of protein production are large, and traditional affinity chromatography processes may require that the fermentation broth is concentrated considerably before the affinity chromatography process. This can harm the desired product and often still results in flow rates for the process that are much larger for the first loading stage than the subsequent elution and/or washing stages.

Multi-column continuous synthesis methods have been developed but these require complex valves and controls to work. They also have the draw back that large volumes of stationary phase need to be used in parallel columns.

BRIEF SUMMARY OF THE DISCLOSURE

In accordance with the present inventions there is provided a method of removing a chemical entity from a liquid: the method comprising:
a) passing an elongate body through a conduit, the conduit comprising a liquid input port and a liquid outlet port; wherein the liquid from which the chemical entity is removed passes along the conduit from the liquid input port to the liquid output port in the opposite direction to the elongate body, the conduit being configured such that the liquid contacts the elongate body; wherein attached to the elongate body is an affinity entity, said affinity entity having an affinity for the chemical entity;
b) washing the elongate body to remove products present having lower affinity for the affinity entity than the chemical entity.

Passing the elongate body through the conduit removes the chemical entity from the liquid. The chemical entity becomes associated (e.g. non-covalently bonded) with the affinity entity that is attached to the elongate body, thus removing the chemical entity from the liquid.

It may be that the elongate body and/or the liquid is subjected to sonication (e.g. ultrasound) as it passes through the conduit. It may be that the elongate body and/or the liquid is agitated as it passes through the conduit.

It may be that the elongate body is passed through a plurality of said conduits. Where the elongate body is passed through a plurality of said conduits, it may be that the liquid is likewise passed through a plurality of said conduits. It may be that the liquid is passed through the plurality of said conduits in the opposite direction to the elongate body. Alternatively, it may be that the liquid is supplied separately to each conduit. It may be that the liquid is supplied separately to each conduit from a single liquid source. It may be that the liquid is supplied separately to each conduit from a plurality of liquid sources. The liquid supplied by each of the plurality of liquid sources may differ, e.g. the concentration of a given reagent in the liquid may vary.

It may be that step b) comprises passing the elongate body through a wash conduit, the wash conduit comprising a wash liquid input port and a wash liquid outlet port; wherein a wash liquid passes along the wash conduit from the wash liquid input port to the wash liquid output port in the opposite direction to the elongate body, the wash conduit being configured such that the wash liquid contacts the elongate body. Passing the elongate body through a wash conduit removes the products present on the elongate body having lower affinity for the affinity entity than the chemical entity. The chemical entity remains associated with (e.g. bonded to) the affinity entity, whilst any other products that were present in the initial liquid are washed off. The products having lower affinity for the affinity entity than the chemical entity will typically be present in (e.g. dissolved in) the wash liquid that is recovered from the wash liquid output port.

It may be that the elongate body and/or the wash liquid is subjected to sonication (e.g. ultrasound) as it passes through the wash conduit. It may be that the elongate body and/or the wash liquid is agitated as it passes through the wash conduit.

It may be that the elongate body is passed through a plurality of said wash conduits. Where the elongate body is passed through a plurality of said wash conduits, it may be that the wash liquid is likewise passed through a plurality of said wash conduits. It may be that the wash liquid is passed through the plurality of said wash conduits in the opposite direction to the elongate body. Alternatively, it may be that the wash liquid is supplied separately to each wash conduit. It may be that the wash liquid is supplied separately to each wash conduit from a single wash liquid source. It may be that the wash liquid is supplied separately to each wash conduit from a plurality of wash liquid sources. The wash liquid supplied by each of the plurality of wash liquid sources may differ, e.g. the concentration of a given reagent in the respective wash liquids may vary.

The method may further comprise step c) recovering the chemical entity from the elongate body. This step might be particularly useful when the desired product is, for example, a protein, a nucleic acid, an antibody, a peptide, a glycopeptide, a glycoprotein or an oligosaccharide.

It may be that step c) comprises passing the elongate body through a displacement conduit, the displacement conduit comprising a displacement liquid input port and a displacement liquid outlet port; wherein a displacement liquid passes along the displacement conduit from the displacement liquid input port to the displacement liquid output port in the opposite direction to the elongate body, the displacement conduit being configured such that the displacement liquid contacts the elongate body. Passing the elongate body through the displacement conduit, displaces the chemical entity from the affinity entity. The chemical entity will typically be present in (e.g. dissolved in) the displacement liquid that is recovered from the displacement liquid output port.

It may be that the elongate body and/or the displacement liquid is subjected to sonication (e.g. ultrasound) as it passes through the displacement conduit. It may be that the elongate body and/or the displacement liquid is agitated as it passes through the displacement conduit.

It may be that the elongate body is passed through a plurality of said displacement conduits. Where the elongate body is passed through a plurality of said displacement conduits, it may be that the displacement liquid is likewise passed through a plurality of said displacement conduits. It may be that the displacement liquid is passed through the plurality of said displacement conduits in the opposite direction to the elongate body. Alternatively, it may be that the displacement liquid is supplied separately to each displacement conduit. It may be that the displacement liquid is supplied separately to each displacement conduit from a single displacement liquid source. It may be that the displacement liquid is supplied separately to each displacement conduit from a plurality of displacement liquid sources. The displacement liquid supplied by each of the plurality of displacement liquid sources may differ, e.g. the concentration of a given reagent in the respective displacement liquids may vary.

It may be that the method further comprises step d) recovering the chemical entity from the displacement liquid that is recovered from the displacement liquid output port. This may be achieved by extraction of the displacement liquid that is recovered from the displacement liquid output port. It may be achieved by performing chromatography on the displacement liquid that is recovered from the displacement liquid output port. It may be achieved by removing any volatile solvent present in the displacement liquid that is recovered from the displacement liquid output port, e.g. by heating and/or subjecting to a vacuum.

It may be that the method further comprises step e) recovering the products having lower affinity from the wash liquid, e.g. the wash liquid that is recovered from the wash liquid output port. This step might be particularly useful when the chemical entity is, for example, an endotoxin and the desired product is one of the products having lower affinity than the endotoxin for the affinity entity. This may be achieved by extraction of the wash liquid comprising said products which a liquid for which the products have a greater affinity than they do for the wash liquid. It may be achieved by chromatography wash liquid comprising said products. It may be achieved by removing any volatile solvent present in the wash liquid from the products, e.g. by heating and/or subjecting to a vacuum.

By using a multistage continuous process each stage can be performed in dedicated apparatus(es) optimised for the flow rates and conditions required for each stage. Thus the number of conduits can be selected such that for example a loading stage could use a longer series of channels to give a longer residence time, and would allow the concentration gradient effect to be fully utilised.

It may be that the elongate body is passed through a plurality of said conduits, a plurality of said wash conduits and a plurality of said displacement conduits.

The method may further comprise: step f) regenerating the affinity entity. It may be that step f) comprises passing the elongate body liquid a regeneration conduit, the regeneration conduit comprising a regeneration liquid input port and a regeneration liquid outlet port; wherein a regeneration liquid passes along the regeneration conduit from the regeneration liquid input port to the regeneration liquid output port in the opposite direction to the elongate body, the regeneration conduit being configured such that the regeneration liquid contacts the elongate body.

It may be that the elongate body and/or the regeneration liquid is subjected to sonication (e.g. ultrasound) as it passes through the regeneration conduit. It may be that the elongate body and/or the regeneration liquid is agitated as it passes through the regeneration conduit.

It may be that the elongate body is passed through a plurality of said regeneration conduits. Where the regeneration body is passed through a plurality of said regeneration conduits, it may be that the regeneration liquid is likewise passed through a plurality of said regeneration conduits. It may be that the regeneration liquid is passed through the plurality of said regeneration conduits in the opposite direction to the elongate body. Alternatively, it may be that the regeneration liquid is supplied separately to each regeneration conduit. It may be that the regeneration liquid is supplied separately to each regeneration conduit from a single regeneration liquid source. It may be that the regeneration liquid is supplied separately to each regeneration conduit from a plurality of regeneration liquid sources. The regeneration liquid supplied by each of the plurality of regeneration liquid sources may differ, e.g. the concentration of a given reagent in the respective regeneration liquids may vary.

During each step, therefore, the elongate body moves or is able to move; for example the movement of the solid phase body may be a movement which would for practical purposes be considered continuous (including continuous movement driven by a stepper motor, which in fact rotates in high frequency steps). In some embodiments, the solid phase body is stationary during performance of a step and then moved on to another apparatus to be subjected to another step. In other embodiments, the solid phase body moves intermittently during performance of a step. The fluid phase flows during at least part of a step and it may flow continuously. Thus, the invention includes embodiments in which the solid phase body is contacted with, e.g. surrounded by, a stream of liquid during part or all of a step. A fluid may flow continuously during a step but in some embodiments fluid flow is discontinuous. In many embodiments, both the solid phase body and the fluid phase move continuously between the beginning and the end of a step.

Affinity Chromatography

The methods of the present invention can be applied in combination with known affinity chromatography techniques. Thus, the options available for the affinity moiety, the means by which it is attached to the elongate body (or a polysaccharide comprised in the elongate body), the wash solution and the means by which the chemical entity can be recovered from the elongate body will be familiar to the skilled person and will be selected based on the identity of the chemical entity. Details can be found in review articles such as Nature Biotechnology, vol 5, December 1987—Large Scale Affinity Chromatography by Yannis D Clonis and Methods; 116 (2017); 84-94—Affinity Chromatography: A versatile technique for antibody purification by S Arora, V Saxena and B V Ayyar, which are incorporated herein in their entirety.

Chemical Entity

The chemical entity may comprise a protein, a nucleic acid, an antibody, a peptide, a glycopeptide, a polysaccharide, an alkaloid, a glycoprotein or an oligosaccharide. The chemical entity may comprise a protein. The chemical entity may be a protein. The chemical entity may comprise an antibody. The chemical entity may be an antibody. The chemical entity may be an alkaloid.

The chemical entity will typically be unchanged by the process. Thus, the species that is recovered from the methods of the invention (e.g. following a displacement step) will typically be the same (i.e. have the same chemical structure) as the species that was present in the initial liquid.

The Liquid

The liquid from which the chemical entity is to be isolated may be a mammalian milk, serum, a fermentation broth, ascetic fluid, hybridoma, a lysate of hybridoma cells, lysate of plant cells, lysate of mammalian cells, lysate of fungal cells, lysate of bacterial cells, lysate of yeast cells, an extract of plant material, an extract of fungal material, a ribosome-produced protein.

Affinity Entity

The affinity entity may be attached to the elongate body via covalent bonding. The affinity entity may be attached to the elongate body via dative bonds and/or hydrogen bonds to functional linker groups that are themselves attached to the elongate body via covalent bonding.

The affinity entity may be attached to the elongate body using a linker group. The linker group is typically a group derived from the reaction of a hydroxyl group on a polysaccharide on the elongate body with a linker agent and reaction of the subsequent species with the affinity entity. Illustrative linker agents include: 1,4-butanediol diglycidyl ether, cyanogen bromide, 1,1'-carbonyldiimidazole, 1,3-dibromo-2-propanol, 2,3-dibromopropanol, divinylsulfone, epichlorhydrin, glyceraldehyde and tresyl chloride.

The affinity entity will be selected based on the chemical entity that is being isolated from the liquid. The affinity entity should have a higher affinity for the chemical entity than for any of the other products that are present in the liquid from which the chemical entity is to be isolated.

The affinity entity may comprise a reactive dye.

The affinity entity may comprise an amino acid. The affinity entity comprise an antibody, peptide, protein, nucleic acid, small molecules, lectin, antigen or anti-antibody Illustrative proteins include protein A, protein G, protein L. Illustrative lectins include concanavalin A, wheat germ agglutinin, mannan-binding protein and jacalin.

The affinity entity may comprise a metal ion, e.g. a transition metal ion. Illustrative metal ions include $Co^{2+}$, $Cu^{2+}$, $Fe^{2+}$, $Ni^{2+}$ and $Zn^{2+}$. Where the affinity entity comprises a metal ion, the affinity entity will comprise a chelating entity covalently attached to the elongate member (e.g. solid phase particles comprised within the elongate member). Said chelating entity will chelate the metal ion. Illustrative chelating entities include phenylalanine tetrazole, iminodiacetic acid, nitrilotriacetic acid and tris(carboxymethyl) ethylene diamine.

The affinity entity may comprise a thioether-substituted organic sulfone (e.g. Thiosorb, T-gel).

The affinity entity may comprise hydroxyapatite.

The association between the affinity entity and the chemical entity is typically reversible. It may be that no covalent bonds are formed between the affinity entity and the chemical entity during step a). The association between the affinity entity and the chemical entity may be hydrogen bonding, dative bonding, ionic bonding, Van der Waals forces or a mixture thereof.

The affinity entity may be pores of a specified size. The pores may simply exclude all products having a size greater than the specified size (the chemical entity having a size below that size). Alternatively, the pores may have a greater affinity for products having a size within a specified range (the chemical entity having a size within that range). Thus, the elongate body may comprise a porous material having pores of the specified size. Examples include porous copolymers, e.g. polystyrene-divinylbenzene. It may be that he affinity entity is not pores of a specified size.

Wash Step

The wash step b) removes any products having lower affinity than the chemical entity for the affinity entity. These products will typically be impurities in the liquid from which the chemical entity is to be isolated that have become absorbed or otherwise associated with the elongate body. The nature of these impurities will depend on how the liquid has been obtained.

Step b) may comprises contacting the elongate solid phase with a wash solution. Said wash solution may be water or an aqueous solution. Step b) may comprise contacting the solid phase with a wash solution, said wash solution comprising a buffer. Additionally or alternatively, said wash solution may comprise a salt (e.g. NaCl or $MgCl_2$). Additionally or alternatively, said wash solution may comprise a detergent.

Displacement Step

In step c) the chemical entity is recovered from the elongate body, typically by displacing the chemical entity from the affinity moiety. Step c) may comprises contacting the elongate solid phase with a displacement solution.

Said displacement solution may be an aqueous solution. It may be a buffer solution (where the wash step b) also used a buffer solution, the buffer solution in step c) will typically be at a different pH to the buffer used in step b)). Additionally or alternatively, said displacement solution may comprise a salt (e.g. LiCl, NaCl or $MgCl_2$). Said displacement solution may comprise guanidine and/or urea.

Said displacement solution may be an organic solvent.

Said displacement solution may comprise an organic chemical having a sufficiently high affinity for the affinity entity to displace the chemical entity. Said displacement solution may comprise imidazole. This is particularly useful where the affinity entity comprises a metal ion.

Said displacement solution may comprise a peptide, protein, antigen, lectin, antibody that has a higher affinity for the affinity moiety than the chemical entity.

The Elongate Body

The elongate body may comprise a polysaccharide, e.g. a cellulose or agarose material which may be cross-linked. Polysaccharide materials comprise hydroxyl groups to which the affinity entity may be attached, either directly or indirectly via a linker group.

The elongate body may comprise a copolymer, e.g. polystyrene-divinylbenzene. Such materials may be porous materials where the affinity moiety is a pore of a specified size. Such materials may have an affinity entity attached to them, e.g. via covalent bonding.

The elongate body may comprise an elongate body portion and a plurality of enclosures distributed along the length of the elongate body portion, said enclosures being formed of a material comprising a chemically inert mesh; and within each enclosure, a plurality of solid phase particles wherein the affinity entity is attached to said particles; wherein the size of the holes in the mesh and the size distribution of the solid phase particles are selected such that the particles do not pass through the mesh.

The term chemically inert is used herein to mean a polymer that is chemically unreactive and/or insoluble in the conditions of the processes of the method.

The mesh may be a polymeric mesh, i.e. one formed of a chemically inert polymer. Polymers such as polypropylene, polyethylene, polyester, polyamide (e.g. aramid), and silk could be suitable. The polymer may be a fluorinated polymer or copolymer. The polymer may be polytetrafluoroethylene (PTFE) or ethylene tetrafluoroethylene copolymer (ETFE). The polymer may be ETFE. The polymer may be aramid. The polymer may be polyether ether ketone (PEEK).

Alternatively, the mesh may be formed of a material selected from glass fibres, titanium, stainless steel, carbon fibre, graphene.

It may be that the material is formed of the mesh, e.g. the polymeric mesh.

The pores of the mesh are typically large enough to allow the liquid and the chemical entity to pass unimpeded or substantially unimpeded through the porous bag or tube to the particles inside. The pore size of the porous material may be less than 150 µm, less than 100 µm, less than 50 µm or less than 25 µm. In certain embodiments, the pore size is in the range from 30 to 80 µm, e.g. in the range from 45 to 65 µm.

It may be that the elongate body and the enclosures are formed of the same material. It may be that the elongate solid phase body comprises two elongate strips of the material connected together so as to form the elongate body portion and the plurality of enclosures. The two strips of material may be connected to each other continuously along both longitudinal sides of the elongate body and periodically connected continuously across the transverse width of the elongate body to form the enclosures. The two strips of material may form part of the same piece of material that is folded along a first longitudinal side of the elongate body. The two strips of material may form part of the same piece of material that is tubular, e.g. one formed on a circular loom.

Where the material is a polymeric mesh, it may be welded continuously along both longitudinal sides of the elongate body and periodically welded continuously across the transverse width of the elongate body to form the enclosures. Where the two strips of elongate material form part of the same piece of material that is folded along a first longitudinal side of the elongate body, the material may be welded continuously along a second longitudinal side of the elongate body and periodically welded continuously across the transverse width of the elongate body to form the enclosures.

Alternatively, the material may be sewn, stapled or bonded continuously along both longitudinal sides of the elongate body and sewn, stapled or bonded continuously across the transverse width of the elongate body to form the enclosures. Where the two strips of elongate material form part of the same piece of material that is folded along a first longitudinal side of the elongate body, the material may be sewn, stapled or bonded continuously along a second longitudinal side of the elongate body and periodically sewn or bonded continuously across the transverse width of the elongate body to form the enclosures.

Where the two strips of elongate material form part of the same piece of material that is tubular, the material may be welded, sewn, stapled or bonded continuously across the transverse width of the elongate body to form the enclosures.

The seams or joins along the longitudinal side or sides of the elongate body may be suitable for providing purchase for a roller, allowing the roller to guide and or drive the elongate material. Thus, the seams or joins along the longitudinal side or sides of the elongate body may comprise sprocket holes or raised or depressed lumps or ridges.

The seams or joins may have a width in the range from 2 mm to 10 mm, e.g. in the range from 3 mm to 5 mm.

The solid phase particles may have a diameter of from 45 to 180 µm, for example from 60 to 180, or from 60 to 100 µm or from 150 to 180 µm. The solid phase particles may be nanoparticles, e.g. nanoparticles supported on an inert solid phase that has the above mentioned diameters or nanoparticles in the form of aggregates.

The elongate body may have a length greater than 500 mm. The elongate body may have a length greater than 1000 mm. The width of the elongate body is typically in the range 5 mm to 100 mm, e.g. 5 to 30 mm. The width of the elongate body may be in the range 15 mm to 25 mm.

The elongate body may be continuous, i.e. it may be in the form of a loop.

The solid phase particles are typically packed in such a way as to allow free movement. This is of benefit when using ultrasound to increase the mixing of a liquid phase and the particles. Thus, it may be that the enclosures are each only partially filled with solid phase particles. It may be that the enclosure contains less than 90% (e.g. less than 80% or less than 70%) of the maximum amount of particles that the enclosure could hold.

The enclosures may have substantially the same transverse width (the dimension of the enclosure in a direction transverse to the elongate body) as the elongate body. There will typically be at least one seam and/or join that runs along the longitudinal edge or edges of the elongate body, said seam or join forming the enclosure. The term 'substantially' in this instance means that the transverse width of the elongate body will be the transverse width of the enclosure plus the sum of the widths of said seam(s) and/or join(s).

The enclosures may have a longitudinal length (the dimension of the enclosure in a direction longitudinal to the elongate body) of between 5 and 50 mm. The enclosures may have a longitudinal length (the dimension of the enclosure in a direction longitudinal to the elongate body) of between 15 and 25 mm.

The enclosures may all be the same size. Alternatively, some enclosures may be smaller than others. This would be useful, for example, for obtaining samples of the solid phase beads at various positions along the elongate membrane, e.g. during operation. It may be there are two groups of enclosures and that the enclosures in each group are the same size as the other enclosures in that group. It may be that the enclosures in a first group are smaller than those in a second group. It may be that less than 20% of the total numbers of enclosures are in the first group. It may be that less than 10% of the enclosures are in the first group. The enclosures of the first group may be situated periodically along the elongate solid phase body.

The solid phase particles are suitable for affinity chromatography. Thus, an affinity entity can be attached to the particles.

The solid phase particles may be spherical. The solid phase particles may be cylindrical. The solid phase particles may be fibres. The solid phase beads may be irregularly shaped.

The solid phase particles may be polymer particles.

The solid phase particles may be a synthetic polymer. Illustrative examples include polystyrene, polymethacrylate (e.g. Separon HEMA®) or a poly acrylamide (e.g. Bio-Gel®).

The solid phase particles may be formed of a natural polymer, typically a polysaccharide material, for example cellulose, dextran or agarose, that may be cross-linked. Illustrative materials include Sephadex®, Superdex®, Sepharose®, Macrosorb®, Trisacryl® and Matrix Cellufine®.

Alternatively, the solid phase particles may be inorganic, e.g. a material selected from controlled porosity glass, porous silica, glass fibre and $TiO_2$.

The affinity entity may be attached to the solid phase particles via covalent bonding.

In a second aspect of the invention is provided an elongate body and attached to the elongate body is an affinity entity. The elongate body and the affinity entity may have any of the features described above for the first aspect of the invention.

Apparatus

The apparatus may be an apparatus as described in WO2017/122009, herein incorporated by reference.

A method of any preceding claim, wherein the method is performed on a system comprising:
an affinity module, said affinity module comprising the conduit; and
a first service module operably connected to a first side of an affinity module, the first service module for supplying and/or receiving the liquid to and/or from the affinity module;
wherein the system is configured for passing the solid phase through the affinity module, via the conduit.

The system may comprise two or more affinity modules, provided in series, such that the solid phase may pass through consecutive affinity modules. It may be that the system is configured such that the liquid also passes through the consecutive affinity modules. It may be that the system is configured such that the liquid passes through the consecutive affinity modules in the opposite direction to the elongate body. It may be that each service module that supplies liquid to the affinity modules is configured to supply liquid from the same liquid source. It may be that two service modules that each supply liquid to the affinity modules are configured to supply liquid from different liquid sources.

The system may further comprise:
a wash module, said wash module comprising the wash conduit; and
a second service module operably connected to a first side of a wash module, the second service module for supplying and/or receiving the wash liquid to and/or from the wash module;
wherein the system is configured for passing the solid phase through the wash module, via the wash conduit.

The system may comprise two or more wash modules, provided in series, such that the solid phase may pass through consecutive wash modules. It may be that the system is configured such that the wash liquid also passes through the consecutive wash modules. It may be that the system is configured such that the wash liquid passes through the consecutive wash modules in the opposite direction to the elongate body. It may be that each service module that supplies wash liquid to the wash modules is configured to supply wash liquid from the same wash liquid source. It may be that two service modules that each supply wash liquid to the wash modules are configured to supply wash liquid from different wash liquid sources.

The system may further comprise:
a displacement module, said displacement module comprising the displacement conduit; and
a third service module operably connected to a first side of a displacement module, the third service module for supplying and/or receiving the displacement liquid to and/or from the displacement module;
wherein the system is configured for passing the solid phase through the displacement module, via the displacement conduit.

The system may comprise two or more displacement modules, provided in series, such that the solid phase may pass through consecutive displacement modules. It may be that the system is configured such that the displacement liquid also passes through the consecutive displacement modules. It may be that the system is configured such that the displacement liquid passes through the consecutive displacement modules in the opposite direction to the elongate body. It may be that each service module that supplies displacement liquid to the displacement modules is configured to supply displacement liquid from the same displacement liquid source. It may be that two service modules that each supply displacement liquid to the displacement modules are configured to supply displacement liquid from different displacement liquid sources.

It may be that the modules (including any affinity modules, wash modules, displacement modules and service modules), are all configured to releasably connect to adjacent modules.

It may be that the first side and further side of the one or more affinity, wash and/or displacement module(s) are each a mating face, and the respective service module has a mating face that is connectable with a respective mating face of each affinity, wash and/or displacement module. It may be that the affinity, wash and/or displacement module(s) is releasably connected to the respective service module.

It may be that the conduit or each conduit (including wash conduits or displacement conduits) comprises a solid phase input port and a solid phase output port. Thus, it may be that one of the solid phase input port and solid phase output port is provided in the side of the affinity, wash or displacement module, and the other of the solid phase input port and solid phase output port is provided in the other side of the affinity, wash and/or displacement module.

It may be that the fluid input port(s) and fluid outlet port(s) are provided on the sides of the affinity, wash and/or displacement module(s) so as to releasably connect and seal to corresponding ports on adjacent modules.

It may be that the system further comprises a holding element, the affinity, wash and/or displacement module(s) and respective service modules being connectable to the holding element.

The system may further comprise one or more service ducting module(s), the affinity, wash and/or displacement module(s) and respective service module(s) connectable to the service ducting module(s), the service ducting module(s) for providing services to the service module(s).

The system may further comprise a solid phase delivery module configured to connect in series with the first service module or affinity module, the solid phase delivery module comprising a source of the solid phase.

It may be that the affinity, wash and/or displacement module(s) comprise a lid portion and a body portion, the lid portion removeable from the body portion so as to give access to the respective conduit, wash conduit and/or displacement conduit.

It may be that the conduit(s) comprise a chamber, and the affinity, wash and/or displacement module(s) comprise a projection that is insertable at least partly into the chamber, the chamber and projection thereby forming a passageway as part of the conduit. Said projection may comprise a roller over which the solid phase may pass.

The system may further comprise a drive train element for moving the solid phase through the system.

The service module(s) may comprise a fluid conduit for connecting with the fluid input port of the respective affinity, wash and/or displacement module(s). The service module(s) may comprise a fluid phase supply or removal element, and the system may further comprise a further service module comprising an electrical power supply element. The service module(s) may further comprise a controller or be connected to a controller, said controller being configured to control at least one of the speed of movement of the solid phase, the speed of movement of the fluid phase, and a process modifying device responsive to one or more sensors. In this instant, sensors include spectrometers or other instruments that can obtain data collected from the fluid phase as it enters the service module.

BRIEF DESCRIPTION OF THE DRAWINGS

Embodiments of the invention are further described hereinafter with reference to the accompanying drawings, in which:

FIG. 1 is a depiction of an illustrative apparatus that can be used to carry out the methods of the invention. It is the apparatus used to carry out Example 2.

DETAILED DESCRIPTION

As used in this specification, the term 'remove' may mean entirely remove or it may mean partially remove. Thus, it may mean that greater than 25% of the chemical entity is removed from the liquid. It may mean that greater than 75% of the chemical entity is removed from the liquid. It may mean that greater than 90% of the chemical entity is removed from the liquid. It may mean that greater than 95% of the chemical entity is removed from the liquid.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

Example 1

Preparation of Immobilized Metal Affinity Chromatography (IMAC) Ribbon

1. Prepare a saturated solution of disodium iminodiacetate in DMF/water 12:5 v/v.
2. Unwind cotton tape (22 mm×1 mm×6 m) from spool and soak in 20 mlg$^{-1}$ of 0.1% v/v detergent in water at 80 C for 1 hour.
3. Wash the tape: 10 min of manual mixing with a glass, using 20 mlg$^{-1}$ of distilled water at 80 C. Repeat five times. Dry the tape at room temperature until touch dry.
4. Dry the cotton by placing into an airtight bottle with DMF and 10% v/v 4 A molecular sieves for 48 hours.
5. Soak DMF-dried cotton tape in anhydrous DMF at 80 C for one hour.
6. Prepare a solution of phosphorous oxychloride (POCl$_3$) in DMF by slowly adding 24 ml of POCL$_3$ to 1 litre of anhydrous DMF.
7. Heat the solution to 90 C using a water bath (exclude moisture from DMF solution!) and add the cotton tape to the solution and continue to heat at 90 C for 30 mins.
8. Remove the tape (should be brown coloured) from the DM F/POCl$_3$ solution and wash twice with DMF.
9. Wash the tape 2× with water.
10. Wash the tape with 5% w/v aqueous NaOH solution.
11. Wash the tape 2× with water.
12. Wash the tape with 5% v/v aqueous acetic acid solution.
13. Wash the tape 2× with water.
14. Place the chlorinated cotton tape into a flask equipped with a reflux condenser, along with an excess of saturated disodium iminodiacetate solution.
15. Heat the solution to 105-110 C for 150 mins with cold water flowing through the condenser.
16. Wash the cotton tape 5× with distilled water.
17. Dry the tape at room temperature for 48 hours or until touch dry.

Example 2

Performing Continuous Chromatography Purification of Lactalbumin from Milk

Skimmed milk was used as a simulant for fermented broth due to milk being very consistent in composition and also having a high concentration of a water soluble protein. A fermented broth may also need ultrasonic treatment (to disintegrate cells and release proteins into solution) and filtration prior to affinity chromatography.

The apparatus 1 used in example 2 is shown in FIG. 1. The cotton tape 2 was passed sequentially through three conduits 3, 4, 5. The conduits were formed from four PTFE blocks 9 that are shaped so as to provide three chambers. Into each chamber was inserted three inserts 6, each insert having at its end a roller 7. The inserts fit into the chamber so as to form three u-shaped conduits 3, 4, 5. The respective liquids flow into each conduit 3, 4, 5 via an inlet (not shown) just below the exit points 10 of the cotton tape 2 into the respective conduits. The respective liquids flow out of each conduit 3, 4, 5 via an inlet (not shown) just below the entry points 11 of the cotton tape 2 into the respective conduits. Rollers 8 were also provided before and after the conduits to help the tape to pass through the apparatus.

1. The functionalised cotton tape 2 is placed into an excess of 1 M aqueous copper sulphate solution and allowed to stand for 30 mins.
2. The cotton tape 2 is then removed from the solution and washed with water until the run off is colourless.
3. Then the tape is passed through the conduit 3, 4, 5 with the first conduit 3 containing a flow of clarified milk whey, the second conduit 4 (the wash conduit) containing a flow of Buffer A (pH 7 phosphate buffer, 20 mM tris(hydroxymethyl)aminomethane, 0.5M NaCl), and the third channel 5 (the displacement conduit) containing a flow of Buffer B (pH 7 phosphate buffer, 20 mM imidazole, 0.5M NaCl)
4. The flow of Buffer B and lactalbumin leaving the apparatus 1 is collected.

The invention claimed is:

1. A method comprising:
    passing an elongate body through an affinity conduit to remove a chemical entity from a liquid, the elongate body comprising:
        an elongate body portion having a length;
        enclosures distributed along the length of the elongate body portion, each enclosure formed of a material comprising a chemically inert mesh with holes, and solid phase particles with a size distribution located within each enclosure;
        an affinity liquid input port; and
        an affinity liquid outlet port;
    wherein:
        the liquid from which the chemical entity is removed continuously passes along the affinity conduit from the affinity liquid input port to the affinity liquid output port in the opposite direction to the elongate body;
        the affinity conduit is configured such that the affinity liquid contacts the elongate body;
        attached to the elongate body is an affinity entity having an affinity for the chemical entity;
        the affinity entity is attached to the solid phase particles; and
        the size of the holes in the mesh and the size distribution of the solid phase particles are selected such that the solid phase particles do not pass through the mesh;
    washing the elongate body to remove products present having lower affinity for the affinity entity than the chemical entity; and
    recovering the chemical entity from the elongate body by passing the elongate body through a displacement conduit to displace the chemical entity from the affinity entity;
    wherein:
        each of the displacement conduit and the affinity conduit are formed in the same body and comprise:
            a chamber; and
            a projection that is insertable at least partly into the chamber;
            such that the chamber and projection form a passageway as part of the respective conduit;
        a displacement liquid:
            is supplied to the displacement conduit separately from a supply of the affinity liquid to the affinity conduit; and
            passes along the displacement conduit from a displacement liquid input port to a displacement output port in the opposite direction to the elongate body:
        the displacement conduit is configured such that the displacement liquid contacts the elongate body; and
        the affinity liquid is different to the displacement liquid.

2. The method of claim 1, wherein one or both the elongate body and the liquid from which the chemical entity is removed is subjected to sonication as it passes through the conduit.

3. The method of claim 1, wherein washing the elongate body comprises passing the elongate body through a wash conduit to remove the products present on the elongate body having lower affinity for the affinity entity than the chemical entity;
    wherein the wash conduit comprises a wash liquid input port and a wash liquid outlet port;
    wherein a wash liquid passes along the wash conduit from the wash liquid input port to the wash liquid output port in the opposite direction to the elongate body; and
    wherein the wash conduit is configured such that the wash liquid contacts the elongate body.

4. The method of claim 3, wherein one or both the elongate body and the wash liquid is subjected to sonication as it passes through the wash conduit.

5. The method of claim 1, wherein one or both the elongate body and the displacement liquid is subjected to sonication as it passes through the displacement conduit.

6. The method of claim 1 further comprising recovering the chemical entity from the displacement liquid that is recovered from the displacement liquid output port.

7. The method of claim 1 further comprising recovering the products having lower affinity from the wash.

8. The method of claim 1 further comprising providing a system comprising:
    an affinity module comprising the affinity conduit; and
    a first service module operably connected to a first side of the affinity module, the first service module for one or both supplying the liquid from which the chemical entity is removed to, and receiving the liquid from, the affinity module;
    wherein the system is configured for passing the elongate body being a solid phase body through the affinity module via the affinity conduit.

9. The method of claim 1 further comprising regenerating the affinity entity.

10. The method of claim 1, wherein the chemical entity is selected from the group consisting of a protein, a nucleic acid, an alkaloid, an antibody, a peptide and an oligosaccharide.

11. The method of claim 1, wherein the affinity entity comprises a metal ion.

12. The method of claim 11, wherein:
the elongate body is a solid phase body; and
recovering the chemical entity from the elongate body comprises contacting the solid phase body with a wash solution comprising imidazole.

13. The method of claim 1, wherein the affinity entity comprises an antibody, protein, lectin, antigen or anti-antibody.

14. The method of claim 1, wherein:
the elongate body is a solid phase body; and
washing the elongate body comprises contacting the solid phase body with a wash solution comprising a buffer.

* * * * *